United States Patent [19]

Janssen

[11] 4,312,500

[45] Jan. 26, 1982

[54] PATIENT SUPPORT

[75] Inventor: Jozef T. A. Janssen, Eindhoven, Netherlands

[73] Assignee: U.S. Philips Corporation, New York, N.Y.

[21] Appl. No.: 125,079

[22] Filed: Feb. 27, 1980

[30] Foreign Application Priority Data

Feb. 28, 1979 [NL] Netherlands ........................ 7901576

[51] Int. Cl.³ ............................................ A61B 13/00

[52] U.S. Cl. ................................................ 269/324

[58] Field of Search ................................ 269/322-325; 5/62, 66-69, 60; 297/90, 322, 316

[56] References Cited

U.S. PATENT DOCUMENTS 4,139,917 2/1979 Fenwick ............................ 269/325

FOREIGN PATENT DOCUMENTS 1940646 2/1971 Fed. Rep. of Germany .

1449483 4/1966 France ........................................ 5/66

293994 7/1928 United Kingdom ..................... 5/69

*Primary Examiner*—Robert C. Watson

*Attorney, Agent, or Firm*—Marc D. Schechter

[57] ABSTRACT

The invention relates to a patient support comprising supporting elements which are connected at facing ends by means of a single coupling rod which is pivotably connected to the ends of the elements. Each element is also pivotably connected, at a location which is situated at some distance from the end connected to the coupling rod, to one of two parallel shafts mounted on a frame. During pivoting of the supporting elements, the length of the supporting surface available for a patient changes, so that a supported patient virtually does not slide at all across the supporting elements during this pivoting movement.

4 Claims, 5 Drawing Figures

PATIENT SUPPORT

BACKGROUND OF THE INVENTION

The invention relates to a patient support, having supporting elements which are pivotably connected to two parallel shafts mounted on a frame. The supporting elements are pivotably interconnected near their facing ends such that by pivoting one element, the other element automatically assumes a position adapted to this pivoting movement.

A patient support of this kind is suitable for examinations, for example encephalographic examinations or fluoroscopy by means of X-rays, as well as for treatment and care of patients.

German Offenlegungsschrift No. 1,940,646 discloses a patient support of the described kind in which the supporting elements are formed by a backrest and a seat to which a leg support is rigidly connected. Near one end, the seat is pivotably connected to one of the shafts mounted on the frame. At the other end, the seat is pivotably connected to an end of the backrest which faces the seat. Furthermore, the seat comprises a rotatable crank disc with two cranks. One crank is connected to the backrest by means of a coupling rod, while the other crank is connected, by means of a second coupling rod, to a second pivot shaft mounted on the frame. Due to this coupling of the backrest and the seat, the seat automatically pivots in the same sense as the backrest when the backrest is pivoted, and vice versa.

The described known patient support is comparatively expensive, because the seat and the backrest are coupled by means of a comparatively large number of movable parts. Moreover, the described known patient support has a drawback in that the seat and the backrest are pivotably interconnected near their facing ends in such a way that they pivot around an axis situated between said facing ends. As a result, the overall length of the supporting surface available for the patient, measured across the seat and the backrest, does not substantially change during pivoting. However, because a patient pivots around an axis which is situated approximately at the hip joint, the length of the side of a supported patient which faces the patient support changes when the seat and the backrest pivot with respect to each other. As a result, the patient will slide across the seat and the backrest of the known patient support. This may be annoying, particularly, for example, during examination of a wounded or sick patient.

SUMMARY OF THE INVENTION

An object of the invention is to provide a patient support in which the length of the supporting surface changes substantially in the same manner as the length of the side of the supported patient, as the patient and support are pivoted. A patient support according to the invention has supporting elements which are mutually pivotably interconnected near their facing ends by means of a coupling rod which is pivotably connected to each facing end. Each supporting element is also pivotably connected to one of two parallel shafts mounted on the frame. The shafts are situated at some distance from the ends connected to the coupling rod.

The supporting elements are pivotably connected to each other by means of a coupling rod which provides a simple and hence comparatively inexpensive construction. Because each supporting element is also pivotably connected to one of the two shafts mounted on the frame, this connection being situated at some distance from the end connected to the coupling rod, pivoting of the supporting elements around these shafts will cause the facing ends of the supporting elements to move apart or towards each other, the angle enclosed by the sides of the supporting elements facing a patient (the supporting surfaces) then decreasing or increasing. Thus, the length of the supporting surface available for a patient, measured across the supporting elements, increases or decreases as the elements are pivoted. As a result, variations in the length of the side of a supported patient which faces the patient support (which variations occur mainly near the hip) during pivoting of the supporting elements with respect to each other are compensated for by the supporting elements Any sliding of the patient across the supporting elements will, therefore, be comparatively insignificant.

A preferred embodiment of a patient support according to the invention is characterized in that one of the supporting elements is pivotably connected to one of the parallel shafts by means of a leg support which is pivotably connected to the end of the supporting element. The leg support is guided, by way of a first journal, in a guide connected to the frame, and it is pivotably connected to the shaft by way of a second journal and a coupling rod. The leg support can be placed in a position which is most desirable for a patient and can be adapted to the position of the supporting elements.

BRIEF DESCRIPTION OF THE DRAWINGS

The invention will be described in detail hereinafter, by way of example, with reference to the accompanying drawing.

DESCRIPTION OF THE PREFERRED EMBODIMENTS

Figure 1:
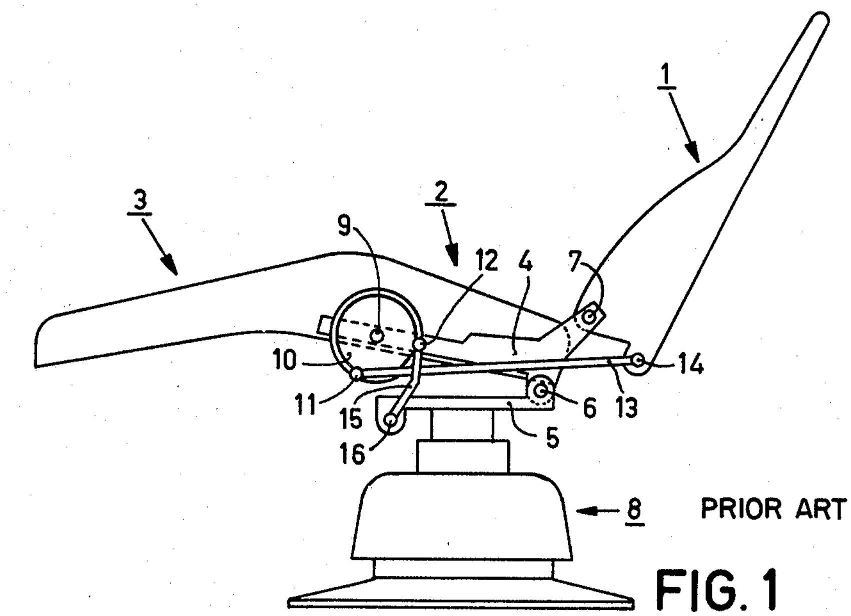
PRIOR ART FIG. 1
FIG. 1 shows a patient support as described in German Offenlegungsschrift 1,940,646.

FIG. 1 shows a patient support, as disclosed in German Offenlegungsschrift No. 1,940,646, comprising supporting elements in the form of a backrest 1 and a seat 2 with a leg support 3 which is rigidly connected to the seat. By means of a supporting frame 4, the seat is pivotably connected to a shaft 6 connected to a frame 5. The backrest 1 is pivotably connected to supporting frame 4 by shaft 7. The frame 5 is mounted on a base 8 which can be adjusted to change the height of the patient support. The supporting frame 4 of the seat 2 further comprises a shaft 9 on which a crank disc 10, with two cranks 11 and 12, is pivotably mounted. Via a coupling rod 13, the crank 11 is connected to a second shaft 14 which is mounted on the backrest 1. Via a coupling rod 15, the crank 12 is connected to a second shaft 16 mounted on the frame. When the backrest 1 is pivoted clockwise around the shafts 6 and 7, viewed in the plane of the drawing, the crank disc 10 is forced by the coupling rod 13 to rotate clockwise around the shaft 9. Consequently, the seat 2 is also forced to pivot clockwise around the shaft 6 by the coupling rod 15. When the backrest 1 pivots counterclockwise, the seat 2 also pivots counterclockwise automatically. Because the seat 2 and the backrest 1 mutually pivot around the shaft 7, the overall length of the supporting surface available for a patient, measured across the seat 2 with leg support 3 and back rest 1, does not change significantly during pivoting. However, a supported patient will slide, because the patient pivots around an axis which is situated substantially at the hip joint, so that the length of the side of the patient which faces the patient support changes during pivoting.

It is to be noted that, as a result of the described coupling of the seat 2 and the back rest 1 by the crank disc 10 and the coupling rods 13 and 15, the torque required for the pivoting of the back rest 1 around the shaft 7 and the torque required for the pivoting of the seat 2 around the shaft 6 at least partly compensate for each other. Adjustment of the supporting elements 1, 2 and 3 of a loaded patient support with respect to the frame 5, therefore, can be performed by hand.

Figure 2:
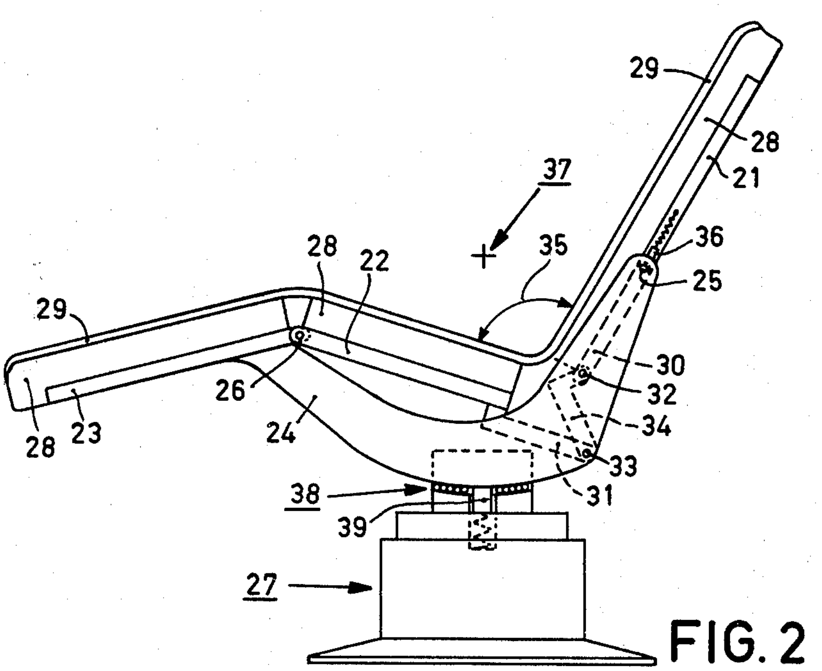
FIG. 2 shows a patient support according to the invention.
Figure 3:
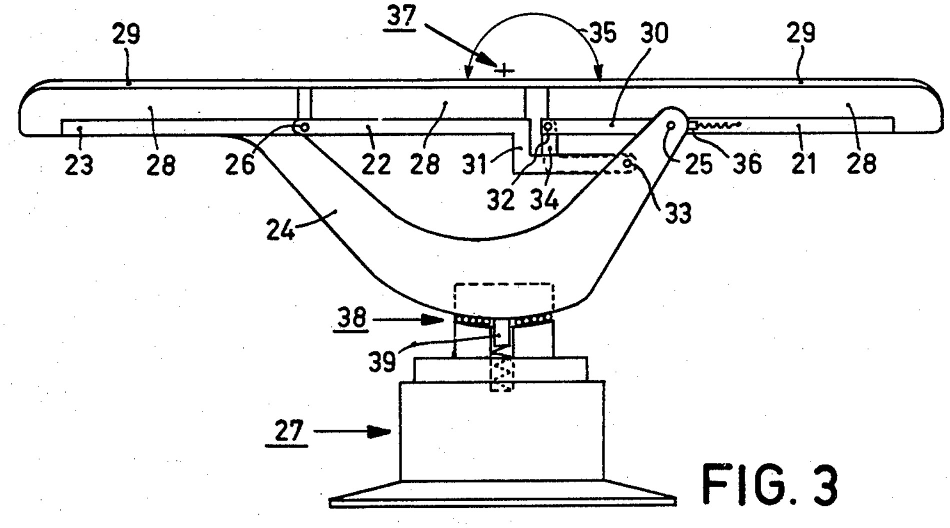
FIG. 3 shows the patient support of FIG. 2 with an angle of 180° between the supporting elements and the support tilted in a horizontal position.

FIGS. 2 and 3 show a patient support according to the invention in different positions. This support comprises a supporting element 21, for supporting the upper part of the body and the head of a patient, a supporting element 22 for supporting the lower part of the body and the thighs of the patient, and a leg support 23. The supporting elements 21 and 22 are pivotably connected to two parallel shafts 25 and 26 which are mounted on a frame 24. The leg support 23 is rigidly connected to the shaft 26 and the frame 24. The frame 24 is mounted, in a manner described below, on a base 27 which can be adjusted to change the height of the patient support. For comfort, the supporting elements 21 and 22 and the leg support 23 are provided with a mattress 28 on each of their supporting surfaces. The assembly of the supports and mattress is covered by a cover 29 of an elastic cloth.

The supporting elements 21 and 22 are also each pivotably connected at facing ends 30 and 31, to a coupling rod 34 which is pivotably connected to shafts 32 and 33. When the supporting element 21 pivots counterclockwise (viewed in the plane of the drawing), the coupling rod 34 forces the supporting element 22 to pivot clockwise; if the supporting element 21 pivots clockwise, the supporting element 22 is forced to pivot counterclockwise.

Pivoting of the supporting elements 21 and 22 around the shafts 25 and 26 causes the facing ends 30 and 31 thereof to move away from or towards each other, the angle 35 enclosed by the sides of the supporting elements facing the patient becoming smaller and larger, respectively. The overall length of the supporting surface available for a patient, measured across the cover 29, then increases or decreases accordingly. As a result, changes of the length of the side of a supported patient which faces the patient support (said changes occurring mainly near the hip in reaction to mutual pivoting of the supporting elements 21 and 22) are compensated for, so that the patient himself will be shifted only a comparatively small amount. In order to fix the mutual position of the supporting elements 21 and 22 after pivoting, the supporting element 21 comprises a brake 36 which acts on the frame 24.

The shafts 25 and 26 are so positioned with respect to the supporting elements 21 and 22 that the center of gravity of the combination formed by the supporting element 21 and the part of a patient supported thereby is situated to the right of the shaft 25 in the drawing. The center of gravity of the combination formed by the supporting element 22 and the part of the patient supported thereby is situated to the right of the shaft 26 in the drawing. As a result, in the case of mutual pivoting of the supporting elements 21 and 22, the torques required for pivoting at least partly compensate for each other due to the coupling by means of the coupling rod 34. Moreover, the center of gravity of the patient support with the patient, diagrammatically denoted by the reference numeral 37, will not be substantially shifted. As a result, the patient support is particularly suitable for tiltable mounting on the base 27 by means of a diagrammatically denoted bearing system 38 with needle bearings which are arranged on an arc of a circle, the center of which is situated at the center of gravity 37 of the patient support with the patient. In order to fix the position of the frame 24 after tilting with respect to the base 27, the base 27 comprises a brake 39 which acts on the frame 24. As a result of the described balancing of the mutually pivotable and tiltable parts, adjustment of the supporting elements 21 and 22 of a loaded patient support with respect to each other as well as with respect to the base 27 can be performed by hand.

FIG. 3 shows the patient support of FIG. 2 with an angle of 180° between the supporting elements 21 and 22 and the leg support 23. The base 27 is tilted to a horizontal position.

Figure 4:
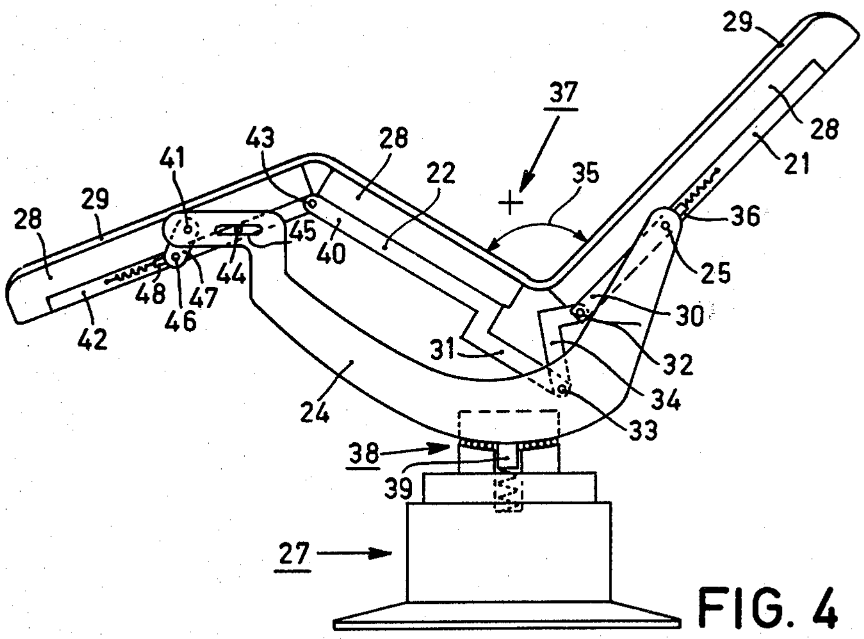
FIG. 4 shows a preferred embodiment of a patient support according to the invention which comprises a leg support which is pivotable with respect to the frame.

FIG. 4 shows a preferred embodiment of a patient support according to the invention, corresponding parts being denoted by the same reference numerals as used in FIGS. 2 and 3. An end 40 of the supporting element 22 of this patient support is pivotably connected, by means of a leg support 42, to a shaft 41 which extends parallel to the shaft 25 and which is mounted on the frame 24. The leg support 42 is pivotably connected to a shaft 43 mounted on the end 40 of the supporting element 22. Leg support 42 is guided, by way of a first journal 44, in a guide 45 which is connected to the frame 24. In addition, leg support 42 is pivotably connected, by way of a second journal 46 and a coupling rod 47, to the shaft 41 mounted on the frame 24. The leg support 42 can be fixed in a position which is most desirable for a patient, and which is adapted to the position of the supporting elements 21 and 22, by means of a schematically shown brake 48 which is mounted on the leg support 42 and which acts on the coupling rod 47. The journal 44 is arranged so that the center of gravity of the combination formed by the supporting element 22 and the part of a patient supported thereby is situated to the right of the journal 44 in the drawing. The center of gravity of the combination formed by the leg support 42 and the part of the patient supported thereby is situated to the left of the journal 44, so that when the elements 22 and 42 mutually pivot around a common shaft 43, the torques required for pivoting at least partly compensate for each other. Moreover, the center of gravity of the patient support with the patient, diagrammatically denoted by the reference numeral 37, will virtually not be shifted.

Figure 5:
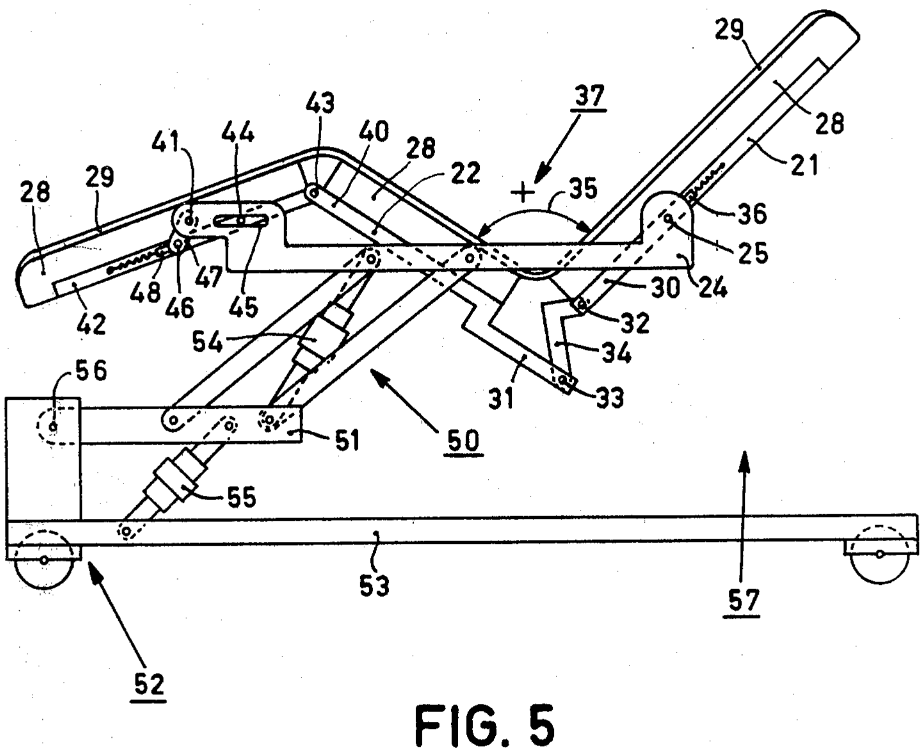
FIG. 5 shows a patient support as shown in FIG. 4 which is used in a patient bed for use in intensive care departments of hospitals.

FIG. 5 shows a patient support of the kind shown in FIG. 4 which is used in a patient bed for use at intensive care departments of hospitals. Corresponding parts are denoted by the same reference numerals used in FIG. 4.

Using a parallel guide 50, the frame 24 is connected to an arm 51 which is pivotably connected, near an end 52, to a mobile bed frame 53. Using for example, a hydraulic drive 54, the height of the patient support can be adjusted. By means of, for example, a hydraulic drive 55, the patient support can be tilted around shaft 56. Because no parts required for supporting are present near the part of the patient bed (which part is diagrammatically denoted by the reference numeral 57 and which is situated opposite the end 52), this part can accommodate equipment, for example for making a radiograph of the patient. The supporting elements 21 and 22, the leg support 42, the mattresses 28 and the elastic cover 29 are made of an X-ray transparent material for this purpose. Radiographs of a patient in a number of medically important positions, for example as desired for intensive care, can thus be made by adjustment of the patient support, without it being necessary to remove the patient from the bed or even without shifting the patient in the bed.

What is claimed is:

1. A patient support comprising:

a frame;

first and second parallel shafts mounted on the frame;

first and second supporting elements each having first and second ends, said first supporting element pivotably connected to said first shaft and said second supporting element pivotably connected to said second shaft such that the second end of one supporting element is adjacent the second end of the other supporting element in at least one position of the patient support, the pivotable connections being at distances away from the second ends; and a single coupling rod having two ends, each end pivotably connected to one of the second ends of the supporting elements.

2. A patient support as claimed in claim 1, CHARACTERIZED IN THAT:

the support further comprises a leg support having an end connected to the first shaft; and the first supporting element is pivotably connected to the first shaft at its first end.

3. A patient support as claimed in claim 1, CHARACTERIZED IN THAT the support further comprises:

a leg support having a journal, the first supporting element connected to the first shaft by means of the leg support, the leg support being pivotably connected to the first end of the first supporting element;

a guide for the leg support journal; and a second coupling rod having two ends, one end pivotably connected to the leg support and the other end pivotably connected to the first shaft.

4. A patient support comprising:

a frame;

a first supporting element having first and second end and having a supporting surface, said supporting surface having a second end which is at a preselected distance from the second end of the supporting element, said first supporting element being pivotably connected to said frame around a first axis;

a second supporting element having first and second ends and having a supporting surface with first and second ends, said second supporting element being pivotably connected to said frame around a second axis which is parallel to the first axis such that the second end of the supporting surface of the second supporting element is adjacent the second end of the supporting surface of the first supporting element in at least one position of the patient support, the pivotal connections to the supporting elements being away from these second ends, and a single coupling rod having two ends, each end pivotably connected to one of the second ends of the supporting elements.

* * * * *